United States Patent [19]

Wislinski et al.

[11] Patent Number: 5,004,579

[45] Date of Patent: Apr. 2, 1991

[54] METHODS AND APPARATUS FOR SELECTIVE PLACEMENT OF FIBROUS MATERIAL IN FORMED FIBROUS ARTICLES

[75] Inventors: Martin Wislinski, Edison; Roger Bergquist, Ringoes; Manfred Schroeder, Freehold; Theodore Weir, Mahwah; Matthew Monetti, Howell; Paul Fung, South River, all of N.J.

[73] Assignee: McNeil-PPC-Inc., Milltown, N.J.

[21] Appl. No.: 359,011

[22] Filed: May 26, 1989

[51] Int. Cl.[5] .......................... D04H 1/72; B27N 3/04
[52] U.S. Cl. .................... 264/517; 264/112; 264/113; 264/115; 425/81.1; 425/82.1
[58] Field of Search ............... 264/517, 518, 113, 115, 264/116, 121, 37, 40.1, 40.4, 112, 118; 425/81.1, 82.1, 83.1

[56] References Cited

U.S. PATENT DOCUMENTS

| | | | |
|---|---|---|---|
| 3,895,089 | 7/1975 | Goyal | 264/518 |
| 4,005,957 | 2/1977 | Savich | 264/518 |
| 4,388,056 | 6/1983 | Lee et al. | 425/83.1 |
| 4,592,708 | 6/1986 | Feist et al. | 425/80.1 |
| 4,598,441 | 7/1986 | Stemmler | 425/81.1 |
| 4,666,647 | 5/1987 | Enloe et al. | 264/121 |
| 4,674,966 | 6/1987 | Johnson et al. | 425/82.1 |
| 4,761,258 | 8/1988 | Enloe | 264/518 |
| 4,764,325 | 8/1988 | Angstadt | 264/113 |
| 4,855,179 | 8/1989 | Bourland et al. | 425/82.1 |
| 4,859,388 | 8/1989 | Peterson et al. | 264/121 |
| 4,915,897 | 4/1990 | Farrington | 264/517 |
| 4,952,128 | 8/1990 | Marshall et al. | 425/82.1 |

Primary Examiner—Mary Lynn Theisen
Attorney, Agent, or Firm—Joseph F. Shirtz

[57] ABSTRACT

Apparatus and methods for forming improved airlaid fibrous articles are disclosed. Airlaying apparatus is provided which permits at least two types of fibrous materials to be defiberized and transported to a single airlaying apparatus. In a most preferred embodiment, a drum-type airlaying drum having a plurality of deposition cavities is provided. By controlling the airflow and pressure differential, selective placement of each type of fibrous material within a cavity is achieved. Also disclosed are improved deposition cavities which permit multiple materials to be airlaid and retained in position by providing a foraminous surface on at least a portion of the cavity sidewall. Most preferably, a hydrophobic fiber layer is formed and a layer of absorbent fiber is deposited within the first layer; the present invention permits a clear demarcation between the fiber types. Also disclosed is improved apparatus for removing airlaid articles from deposition cavities, using a precisely controlled airstream. Improved methods of making airlaid articles by regulating process parameters and using the improved apparatus of the present invention are also disclosed.

27 Claims, 4 Drawing Sheets

METHODS AND APPARATUS FOR SELECTIVE PLACEMENT OF FIBROUS MATERIAL IN FORMED FIBROUS ARTICLES

The present invention relates to methods and apparatus for selectively placing one or more fibrous materials within a formed article. More specifically, the present invention permits different types of fibrous materials to be formed into an absorbent core for product such as a sanitary napkin, diaper or the like.

BACKGROUND OF THE INVENTION

The ongoing research into the chemistry of absorbent materials, particularly fibrous materials such as cellulose, has yielded significant gains in the affectivity of absorbent products. Improvements in the absorptivity, fluid retention and other characteristics which affect user comfort, such as decreased stiffness, have all been realized. Additionally, it has been found that certain absorptive materials may be treated on line to render them hydrophobic or fluid repellent to some extent. Most absorbent products have at least one major surface which is exposed to a fluid flow or a collection of fluid. Hydrophobic materials may be combined with absorbent materials to provide a structure which absorbs and retains fluids, while preventing exudation of the retained fluids from the lateral sides of the pad, or by providing a layer which prevents the fluid from completely traversing the pad from the absorbing major surface to another surface.

Along with advanced materials and improved absorbent article structures comes the concomitant need for advanced manufacturing techniques. This is particularly true regarding items such as sanitary napkins, disposable diapers, wound dressings and the like, which are produced in necessarily extremely high volumes. In many instances, the materials which comprise such absorbent articles are manufactured in sheet form. In other instances, the materials may be in pellets or randomly sized pieces, however, they are usually not initially comprised of individual fibers. Accordingly, apparatus and methods have been developed whereby the starting materials are ground or otherwise physically impacted to render the material into a fibrous state, this process is known as "defiberizing". For example, wood pulp may be defiberized in a conventional hammermill, disk mill or lickerin. The defiberized material is then readily formed into absorbent articles having a high level of consistency.

It has been found that an efficient way of handling defiberized material for mass producing absorbent articles is by creating an air-entrained stream of the defiberized material. Using this technique, the material may be efficiently transported and handled in high speed production machinery. Air-entrained defiberized material may be formed into absorbent pads or the like by passing the airstream through a foraminous surface; if the foramen are of the proper size, the defiberized material is deposited thereon, this process is know as "airlaying". Most typically, apparatus may be constructed which comprises an air entrainment system which delivers a stream of fibers to a rotating drum. Disposed on the periphery of the drum are a series of foraminous cavities or molds, usually substantially in the shape of the desired article. In certain cases, however, the periphery is a continuous foraminous surface, allowing the production of a continuous airlaid sheet. Fibers are then airlaid on the foraminous surface; in some instances, if the cavity is overfilled, the excess is removed by passing the cavity in close proximity of a rotating brush, a process known as "scarfing". By regulating the internal pressure of the drum, relative to the pressure of the air-entrained stream, the density of the deposited fibers can be controlled. Additionally, in certain apparatus a positive pressure is created in portions of the drum, allowing the airlaid articles to be ejected for further processing.

An air-drum type apparatus for forming fibrous pads from a sheet of fibrous material is disclosed in U.S. Pat. No. 4,005,957—Savich. The apparatus described therein consists of a means for defiberizing a sheet of fibrous material and providing a stream of air-entrained fibers to a rotating drum. A series of foraminous cavities are disposed on the periphery of the drum, into which the air-entrained fibers are introduced, producing an airlaid article in the shape of the recess. Savich teaches the forming of the article in a curved recess and ejecting the airlaid article onto a flat vacuum conveyer, thereby providing an article with one curved side and one flat side. The pressure differential between the vacuum conveyor and the rotating drum is sufficient to compress the airlaid article into an article having a relatively greater basis weight.

Another example of airlaying apparatus is presented in U.S. Pat. No. 4,598,441—Stemmler, which discloses apparatus for the manufacture of absorbent pads shaped to fit the body. As discussed above, it is sometimes desireable to produce absorbent articles comprised of two or more materials. Stemmler teaches the use of what is essentially a series of two separate, identical forming machines connected by a transfer wheel. An air-entrained fiber stream is created from a cellulose web using separate apparatus attached to each machine. The first machine has a hollow drum having recesses into which a stream of air-entrained fibers is carried. The air-entrained fibers are deposited to form a first component layer of the absorbent article. The first layer of the article is then transferred to the second machine where the second layer of the article has been formed using a second stream of fibers. The two layers are pressed together by a transfer drum which transports the resulting two-layer article to be further compressed and ejected. Thus, Stemmler teaches the formation of a two layer article, each layer of which may be comprised of a different fibrous material. The reference teaches the placing of a first airlaid layer and a second airlaid layer of substantially the same shape and surface area atop one another, and compressing the layers to form an absorbent article.

An apparatus which incorporates apparatus for defiberizing a web of compressed material and forming the resulting fluff into absorbent pads is disclosed in U.S. Pat. No. 4,674,966—Johnson, et al. (Johnson I). A hammermill creates fluff, which is drawn by a vacuum shroud through insert molds which form the fluff into a desired shape. The molds are arrayed on a circular drum; any overfill is removed and recycled as each mold exits the drum. The molds illustrated are straight-sided and have a foraminous bottom surface, beneath which is disposed structure for controlling the airstream carrying the fibers.

The use of multiple streams of air-entrained fibers is taught by British Patent Application No. 2,191,793. The disclosure is primarily directed toward splitting streams of air-entrained fibers in a clump free manner. Such split streams are used to form absorbent articles having a central core of super absorbent, overlaid by a larger layer of fibers. It is important to keep the materials used for deposition free of clumps or other irregularities in order to assure a consistent product and an uninterrupted, continuous manufacturing process. The British reference teaches the use of two separate drum-type airlaying apparatus. In one of the airlaying drums, the air-entrained fibers are mixed with a superabsorbent prior to deposition in order to form the superabsorbent core. Separate pad layers produced by each airlaying apparatus are joined by compressing one atop the other using conveyor belts and other transfer apparatus external to the airlaying machines.

U.S. Pat. No. 4,592,708—Feist discloses apparatus for making airlaid articles of non-uniform thickness. The device disclosed therein is a drum-type airlaying apparatus for making discrete absorbent fibrous articles of airlaid matter. Feist utilizes a rotating deposition drum having a plurality of article formation cavities disposed in circumferentially spaced relation about the periphery of the deposition drum. Each of the cavities has a foraminous bottom wall. By providing means for directing air-entrained fibers toward the periphery of the drum and means for vacuum drawing the entrainment air through the foraminous bottom walls and exhausting it from the apparatus, discrete absorbent articles are obtained. The improvement provided by Feist consists of directing the stream of fibers substantially radially toward the drum, thus assuring deposition on the bottom of the forming cavity. Feist also teaches exhausting the entrainment air through substantially empty additional cavities disposed upstream from the cavity into which the fibers are being deposited.

In addition to airlaying apparatus generally, the control of the impinging air-entrained stream of fibers has been usefully exploited. It has been found that it is easier to regulate the deposition of airlaid fibers by regulating open area of the foraminous deposition surface and, concurrently or separately, regulating the pressure and/or velocity at or near the point of deposition. In this regard, it has been found that a variety of screens or baffles may be used to achieve certain useful conditions when such apparatus are placed beneath the foraminous deposition surface, that is, when the deposition surface is disposed between the impinging airstream and the regulating apparatus.

For example, U.S. Pat. No. 4,388,056—Lee et al. discloses apparatus for continuously making an airlaid fibrous web having a patterned basis weight distribution. The contoured web produced has alternately spaced relatively high basis weight and relatively low basis weight regions. Lee et al. teaches the use of air flow modulating means which can be adjusted to produce a range of pressure differentials across the foraminous bottom surface of the recess into which air-entrained fibers are introduced.

Also, West German Patent DE 3 5 08 344 A1 discloses a web forming assembly for use in a drum-type airlaying apparatus. A series of apertures are disposed along the bottom surface of the assembly, which is contoured to produce a pad having a central portion of a somewhat greater thickness than the remainder of the article formed. The cavities in the deposition drum are subdivided into a number of zones, each zone having a separate, regulated vacuum line. The device disclosed permits the production of airlaid articles of uniform quality having a varying thickness.

An apparatus and process having airflow regulating means is disclosed in U.S. Pat. No. 4,666,647—Enloe et al. (Enloe I). The improvement of Enloe I lies providing apparatus for the formation of laid fibrous articles having a non-stepwise gradation in basis weight. Enloe I teaches the use of a concave forming surface bounded by angled walls, whereby the laid fibrous article is readily removable from a foraminous forming surface. As shown in FIGS. 2 and 3 of Enloe I, the foramen are located on both the bottom and the sides of the recess into which the air-entrained fibers are laid.

Similarly, U.S. Pat. No. 4,761,258—Enloe (Enloe II) discloses apparatus for forming of airlaid fibrous webs. The webs disclosed have tailored absorbency zones, wherein certain areas have a higher basis weight, and therefore a higher absorbency. Enloe II teaches depositing air-entrained fibers on a foraminous web forming structure. A gas flow regulating means using apertures provides a selected pattern of gas flow resulting in a web forming assembly which creates a desired distribution of fiber basis weight across the formed web.

Finally, European Patent Application No. 85300626.0 (publication no. 151033) discloses methods and improved apparatus for making discrete airlaid absorbent articles. A drum-type apparatus is disclosed, having a series of cavities which have foraminous bottom walls. As shown in FIG. 2, the foraminous bottom wall is preferably a contoured mesh structure, having a relatively uniform distribution of the foramen. The airlaid articles are then further processed after deposition. The articles are compacted a predetermined amount and then ejected, the compaction means is shown as comprising a lugged wheel in gear-like engagement with the cavities of the airlaying drum.

Also known in the art is the separation of fluff components. For example, U.S. Pat. No. 4,625,552—Johnson (Johnson II) discloses an instrument for separating out any one or more of the components of any given sample of fluff. As pointed out by the reference, "fluff" is a collection of wood pulp fibers which, if recycled, during a production process may also include bits of reclamation waste, such as plastic or other materials. Although Johnson II is primarily directed toward testing apparatus for determining the composition of a sample of fluff, one of ordinary skill is also taught how to construct apparatus which can separate out any one or more of the components of the fluff. To accomplish this result, fluff is agitated by compressed air and loose fibers are separated and drawn through a sieve by a vacuum, while the non-fiber portions of the fluff are left in an agitation chamber. The fibers are caught in a sieve, while the highly defiberized, broken fibers are caught later downstream in a filter.

Thus, although several variations of airlaying apparatus and deposition control are known, it would be desireable to provide apparatus capable of continuously depositing two or more materials in selected areas of a product. At present, such constructions are limited to placing a first layer atop a second layer and compacting the resulting assembly. Such a construction is not preferred, however. In the case of many absorbent articles, such as those combining absorbent and repellent fibers. It would be further desireable that apparatus be constructed which required only a reduced the cost and complexity of the airlaying equipment, while still allowing two or more materials to be continuously deposited. Finally, such apparatus would ideally be flexible to the extent that the characteristics of the product and the geometry of the areas in which materials are selectively deposited may be easily changed.

SUMMARY OF THE INVENTION

Accordingly, it has now been found that apparatus for forming fibrous articles having at least two distinct portions of fibrous materials may be constructed. Such apparatus comprises a first mill and a second mill for defiberizing two distinct materials. The defiberized materials are then air-entrained and transported to first and second airlaying locations. The airlaying locations are located so as to be in communication with airlaying apparatus. In a most preferred embodiment, the airlaying apparatus comprises first and second forming chambers in communication with a duct means carrying first and second air entrained fibers or other material to be deposited. A cavity transport device having an interior section in which a vacuum is created is also provided; most preferably this device will be of the rotating drum type. Disposed upon the periphery of the transport device are a plurality of deposition cavities, at least a portion of each of the deposition cavities has a foraminous surface. Disposed in the interior section of the cavity transport means, is a vacuum chamber, in communication with at least a portion of the foraminous surface of a deposition cavity. The system utilizes air handling apparatus to create controlled pressure differentials between the airlaying locations and the interior section of the cavity transport means. In operation the first defiberized material is deposited in at least a portion of a deposition cavity and the second defiberized material is deposited in at least a portion of a deposition cavity resulting in an article having at least two distinct portions of fibrous materials. After the article is formed it is removed, most preferably by a carefully controlled stream of compressed air while simultaneously being transferred to a vacuum belt or drum.

In certain embodiments, the apparatus described is also provided with environmental control equipment to regulate the temperature and humidity within the duct means, this is important when one of the fibers being deposited is hydrophobic, in order to ensure proper defiberization and prevent agglomeration throughout the system. Also provided in certain embodiments is scarfing equipment for removing airlaid material extending beyond the boundaries of the deposition cavity, prior to the ejection of the fibrous article.

In the present invention, the separation between the layers of different materials is largely maintained by the novel basket screen mold disclosed. By carefully controlling the positive and negative pressures beneath the foraminous bottom surface of the basket, it has been found that a first material may be airlaid in a defined area and retained there while a second material is airlaid in another defined area. The basket screen mold and related apparatus provide a series of baffles underneath the mold for controlling the airflow and a portion of "honeycomb" material which reduces the turbulence and helps eliminate side currents which may lead to undesirable clumping.

Methods of producing airlaid articles of two or more clearly defined layers or portions are also provided.

DETAILED DESCRIPTION

As discussed above, it is known in the art to use a forming chamber that deposits defiberized material into a molding cavity in either a flat or contoured configuration. However, the system of the present invention delivers multiple defiberized materials and/or particulate components into different zones of the same molding cavity for the production of an improved sanitary protection product, sanitary napkin, diaper and the like.

The apparatus and methods of the present invention allow the deposition of two or more materials in a manner such that the resulting product is not limited to being formed from two "layers" of different material. Instead, the capability is provided to selectively deposit fibers of different characteristics in a variety of depths and configurations. Most preferably, a "cup" of hydrophobic fibers is disposed on one side and along the edge of a central "core" of absorbent fibers. When the absorbent core is placed against the body, such a construction will absorb fluids through the core, but the hydrophobic "cap" will prevent flowthrough or exudation from the front surface and lateral sides of the article. These novel improvements of the present invention mainly relate airlaying apparatus of the type of using auxiliary defiberizers and fiber or particle metering devices that deliver different materials to specific locations along the forming drum. The resulting process is known as "selective placement".

Figure 1:
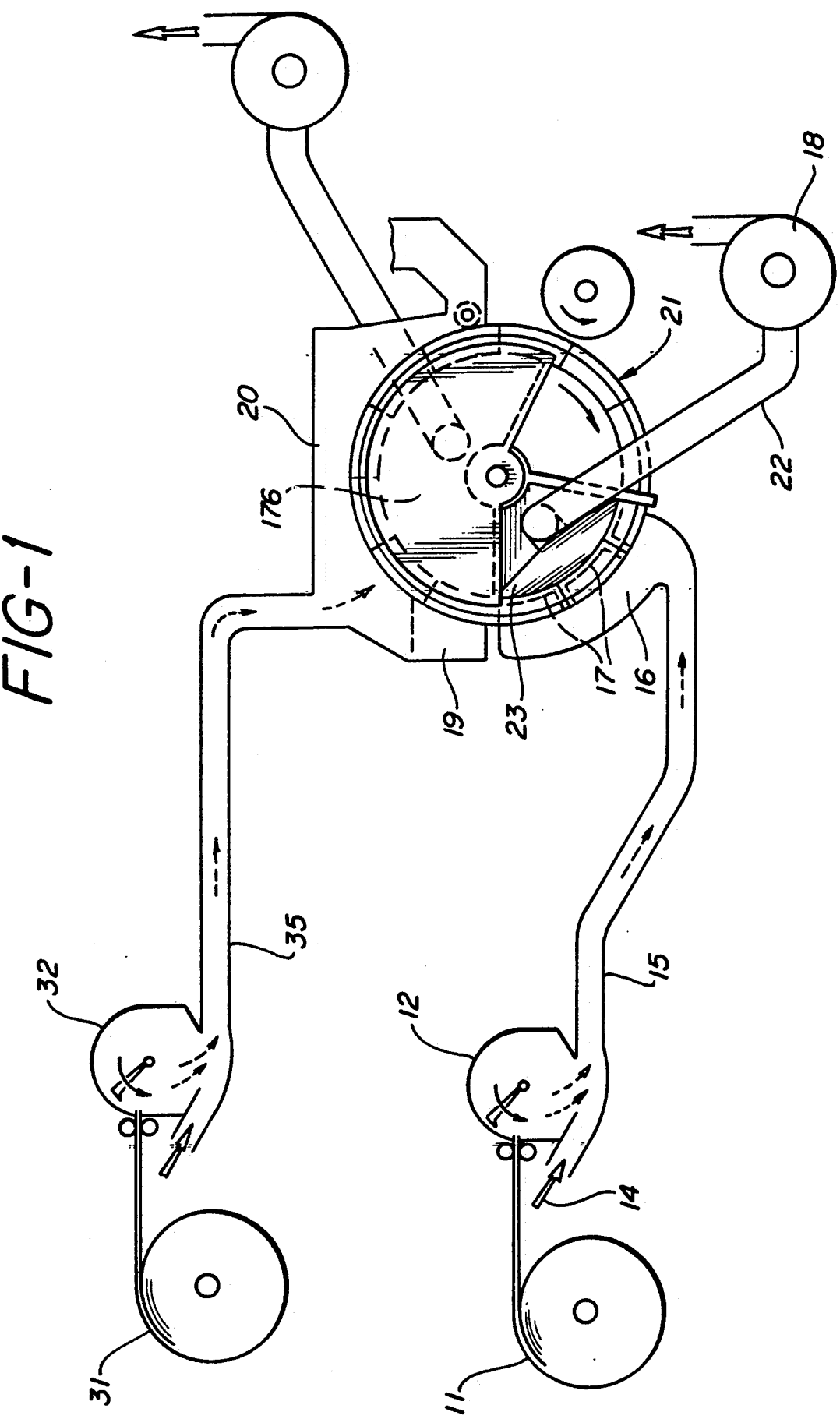
FIG. 1 is a partial diagrammatic view of the preferred airlaying apparatus of the present invention.

Referring to FIG. 1, there is illustrated a diagrammatic representation of a preferred apparatus for practicing the present invention. Certain details, such as electrical and vacuum lines, have been omitted in order to simplify the description. Those of ordinary skill are well versed in such aspects of airlaying and similar apparatus. A first type wood pulp or other fibrous material 11 is defiberized in a conventional hammermill, disk mill or lickerin 12, and fed into an air-entrained stream moving in an air duct 15. The air-entrained stream of a first defiberized material moves to a first forming chamber 16 which is preferably directly adjacent to a molding cavity 17. The molding cavity 17 is preferably one of a plurality of such cavities disposed on the periphery of the deposition drum 21 of a rotating drum-type airlaying device. However, other airlaying apparatus may be substituted quite readily. For example, an enclosed conveyor carrying mold cavities which has a sufficient interior vacuum could also be used. As will be further understood by those of ordinary skill, the feeding of defiberized materials to the deposition drum 21 is accomplished either by directly feeding the materials to a forming chamber from the underside of a mill or by conveyance through duct work.

A vacuum source 18 directs the defiberized materials into the molding cavities 17 along the periphery of the rotating deposition drum 21.

As shown, a duct 22 connects a first forming chamber 16 to the vacuum source 18. In some versions of this device, deposited materials overfill the molding cavity 17 slightly and are scarfed and recirculated back into the forming chamber. The fabricated absorbent cores are then deposited onto a transfer drum, discussed below, and become available for further processing into a finished product. The construction of vacuum sources and the other equipment disclosed herein is generally known to those of ordinary skill; further elaboration being unnecessary at this junction.

Also depicted in FIG. 1 is a second defiberizing and air-entrained system. A second fibrous material 31 is defiberized by a second hammermill 32 or similar apparatus. The defiberized second material is transported via a duct 35 to a second forming chamber 20, disposed at a fixed location on the deposition drum 21. The equipment described relating to the second fibrous deposition may be of the conventional type described above. Moreover, other equipment or materials may be substituted. For example, it may be desired to deposit a foam or other material, rather than a second fibrous material.

It is understood by those of ordinary skill that although in a most preferred embodiment a hydrophobic layer of fibrous materials will be airlaid first, followed by a layer of absorbent material, the present apparatus is not limited to the manufacture of this type of construction. The present invention permits the formation of an article having two or more layers, portions or sections which are comprised of materials having different characteristics. Advantageously, the present invention facilitates the production of such articles at a high rate of speed and further permits the layers to be clearly demarcated.

One aspect of the present invention comprises a novel enhancement to a molded core production system as described immediately above. The system of the present invention uses one or more auxiliary formation chambers along the main formation drum for specialty absorbent core production. The absorbent cores produced have fibers of two or more types selectively placed in distinct areas of the article. Referring again to FIG. 1, there is illustrated a preferred system for pulp delivery. A specially designed scrub chute 13 located under the first mill 12 transitions the selected materials out of the mill and into an air stream 14 in a uniform manner which substantially reduces the agglomeration of the fibers. The defiberized air-entrained material is then transported via conventional ductwork 15 to an airlaying apparatus. A contoured formation chamber 16 of specific geometry deposits the individual fibers into the mold cavity 17; the details of the formation chamber 16 are discussed below. A specially designed mold, also discussed below, channels the defiberized fibers into selected locations within the confines of the mold cavity 17. A neutral zone 19 located after the first formation chamber 16 is provided to isolate the stages of the deposition processes.

Specialty materials, most preferably a repellent or hydrophobic pulp, are preferably defiberized in a screenless hammermill 12 which is rotating between about 5,000 to about 7,000 RPM, most preferably about 6,000 RPM, with a peripheral tip velocity of about 13,600 ft/m to about 19,000 ft/m most preferably about 16,900 ft/m. However, other defiberizing apparatus may be used. To prevent clumps forming at the defiberizer, it has been found that throughput should be less than about 40 lbs/hr/in. of hammermill width. Material which has been defiberized and influenced by the vacuum from the auxiliary vacuum source 18 is now transported into the scrub chute 13 and mixed with conditioned air 14, preferably with a relative humidity (RH) between about 50% RH to about 75% RH, and most preferably about 65% RH. The humidity requirement is critical to the transportation of repellent fibers, due to the moisture resistance of such fibers relative to conventional absorbent pulp. A high static charge is developed in the defiberization and transportation of these fibers; humidified air reduces agglomeration and increases fiber deposition uniformity. Therefore, the air quality within the entrainment apparatus must be controlled. The fibers, once treated with humidified air, are transported through conventional ductwork, preferably at a velocity of about 3,000 to about 15,000 ft/min, and most preferably about 6,000 ft/min. It will be understood, however, that velocity is dependent upon both materials and the position within the system. The velocity will vary widely throughout the system, but will be within a specified range. In other embodiments or for the purposes of making products having other than a repellent fiber layer, the relative humidity may be less critical, although it may still be controlled to some degree.

The defiberized, humidified repellent fiber material then enters the formation chamber 16 which is contoured to efficiently deposit the transported fibers into the open mold cavities 17. The exact curvature of the formation chamber depends upon the materials being deposited and the conditions under which the deposition takes place. By varying the velocity, pressure and angle of impingement, those of ordinary skill will be able to achieve the results contemplated herein with a minimal amount of experimentation. Further details of the formation chamber 16 are discussed below with reference to FIG. 2. Forming pressures in the forming chamber 16 preferably range from about $-3''H_2O$ to about $-15''H_2O$ and most preferably the pressure is about $-10''H_2O$. Differential pressures through the mold cavity preferably range from about $-17''H_2O$ to about $-60''H_2O$ and most preferably is about $-41''H_2O$. Fibers deposit themselves into select locations within the cavity due to the chambering of the mold and the corresponding baffling located under the mold cavity 17, which is discussed in greater detail below. The deposition uniformity is controlled by the precise control of material infeed, humidity control, air transportation velocity control, and forming chamber geometry. The mold cavities 17 move through the formation chamber 16 and pass into the neutral zone 19 where a pressure differential through the mold preferably between about $-25''H_2O$ and about $-45''H_2O$ is placed across the mold, with the neutral chamber preferably having a pressure of about $0''H_2O$ to about $-5''H_2O$. This neutral zone 19 separates the deposition chambers 16, 20 and preferably has a length from about 10% to 500% and most preferably about 100% of the pitch length of the mold cavity 17.

The mold cavity 17 then moves through the neutral zone 19 into the next deposition zone 20 where it is processed by depositing air-entrained defiberized material in the conventional manner. Ultimately, a complete molded core is transferred out of the mold cavity 17 and out of the vicinity of the airlaying apparatus for further processing. As discussed above, those of ordinary skill will readily appreciate the variations of the process described. For example, the "cup" of fibers which is formed can be filled with a hydrophilic foam, rather than absorbent fibers, therefore the second deposition chamber 20 would be of a somewhat different design.

Figure 2:
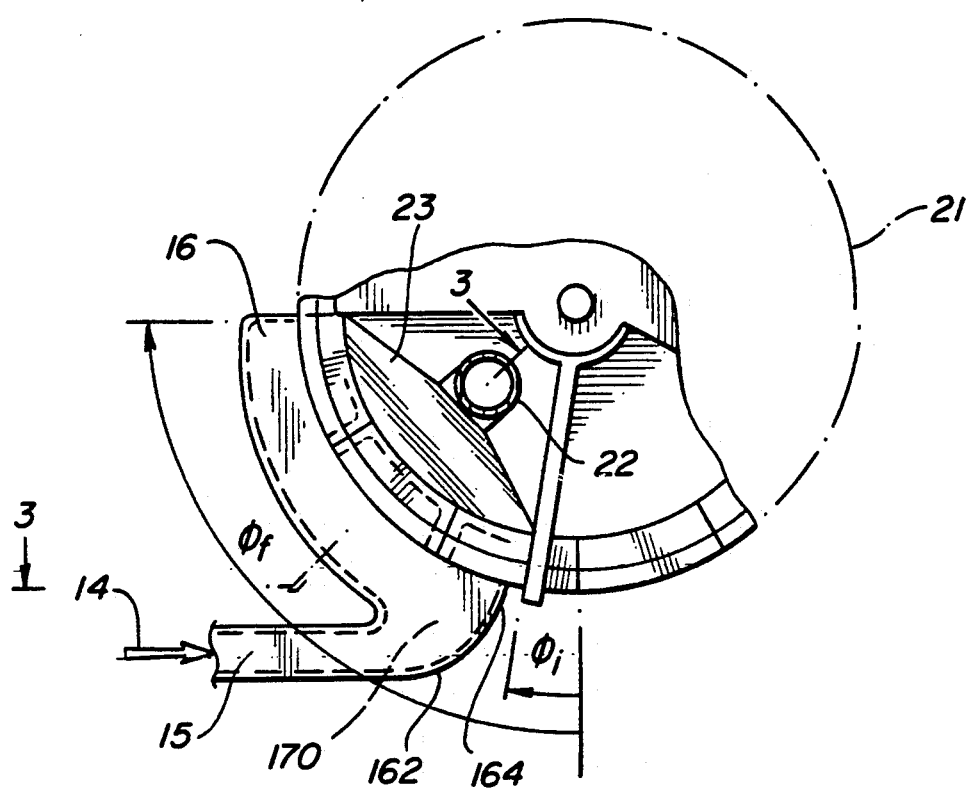
FIG. 2 is a partial diagrammatic view of a deposition chamber and airlaying drum made in accordance with the present invention.

Referring now to FIG. 2, there is illustrated a preferred embodiment of a formation chamber 16 for use in the present invention. As explained above with reference to FIG. 1, a stream of air 14, carrying fibers or other materials to be deposited within a mold cavity, is conveyed in a duct 15 to the forming chamber 16. An elbow 162 with a rectangular cross-section is located just prior to the formation chamber 16. The radius of curvature of the elbow is on the opposite side of the duct from empty molds entering the formation chamber 16. The action of the elbow 162 on the conveyed materials is to concentrate the materials toward the straight wall 164 resulting in a rapid deposition of the material into the mold cavity 17. The side walls of the elbow 162, the interconnecting duct 170 and the forming chamber 16 are preferably the same distance apart; the distance is most preferably substantially the width of the mold cavities 17.

Figure 3:
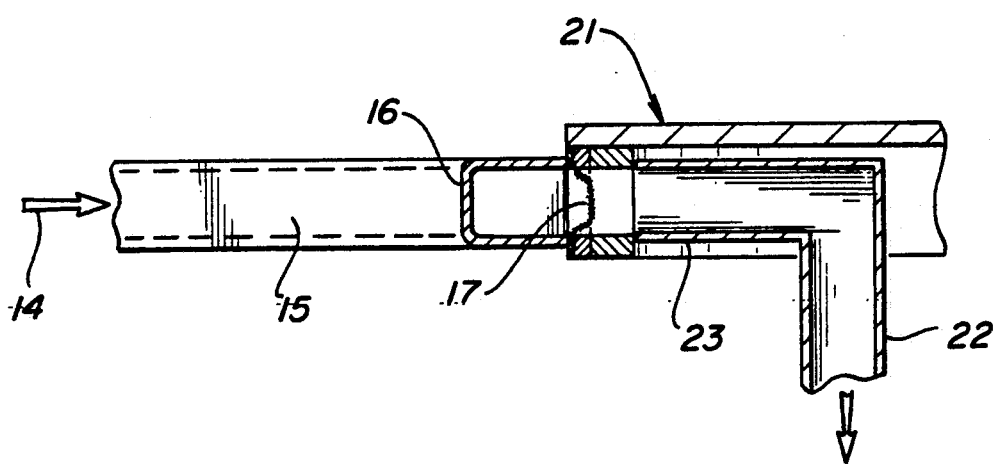
FIG. 3 is a cross-sectional view, taken along line 3—3 in FIG. 2 of a portion of a preferred deposition chamber.

As a mold cavity 17 enters the forming chamber 16 at the intersection with the deposition drum 21, air is drawn through the mold cavity 17 into the vacuum chamber 23. As shown in FIG. 3, the vacuum chamber 23 is connected to a vacuum source 18 (not shown) via duct 22. A foraminous surface in the mold cavity 17 traps the conveyed air-entrained material. Referring again to FIG. 2, as the mold cavity 17 continues to rotate from $\phi_i$ through $\phi_f$, less and less air is drawn through the mold, due to build-up of deposited material on the foraminous surface of the mold cavity 17. The average amount of air flow through the deposition drum 21, as a function of $\phi$, is determined by testing the cross-sectional area, $A_{100}$, of the forming chamber which continually decreases with the angle $\phi$ to maintain air velocity (at least about 3000 ft/min) in the forming chamber.

The suction chamber 23, as shown in FIG. 3, is disposed on the inside of the deposition drum 21, and extends from $\phi_i$ to $\phi_f$, as shown in FIG. 2. The width of the suction chamber 23 is substantially the width of the flow passages in the mold cavities 17, as shown in FIG. 3.

In conventional forming chambers, poor control of air velocity (magnitude and direction) causes vortices within the chamber, which may agglomerate fibers into low density clumps. Edges within the chambers cause buildup of low density clumps which erratically break loose and fall into the mold cavities. These low density clumps lower the integrity of the absorbent product, increasing wet collapse and reducing wicking—all of which are undesirable characteristics. Moreover, due to poor air velocity control (magnitude and direction), conventional forming chambers use about twice the forming air volume as the chamber 16 of the present invention. Therefore, the present invention requires smaller vacuum sources, air conditioners and dust collectors, resulting in greater energy efficiency and more economical operation.

Another advantage of the distribution chamber of the present invention are that molds are filled rapidly since most of the material is deposited early in the molding cycle. Since the design eliminates air recirculation and edges within the chamber which may cause agglomeration, clumps and uneven filling of the mold cavities is substantially eliminated. The design minimizes the amount of air necessary for conveying and molding, however, the material is deposited with high kinetic energy onto the screen, resulting in a higher density product, thereby enhancing the integrity of the molded product.

The present invention also provides novel means for selectively placing fibers and other materials within the core of an absorbent product, such as a sanitary napkin. The invention permits multiple layers, strips, rings and other geometric shapes of fibers and particles to be placed in a mold cavity and be built up, one on top of the other, or side by side, until the mold cavity is filled. This allows specialized materials to be placed and used optimally within the core of an absorbent product.

Figure 4:
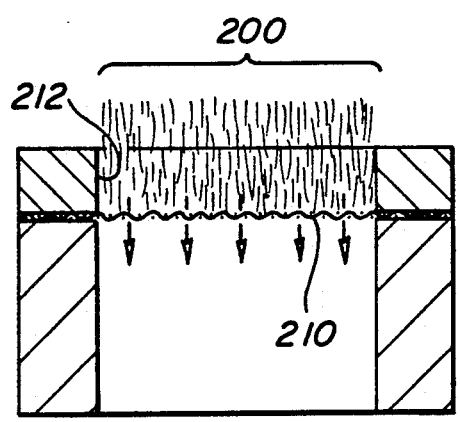
FIG. 4 is a cross-sectional view of the improved mold cavity and screen found in prior art airlaying apparatus.

As depicted in FIG. 4, in conventional molding processes, air and entrained material 200 is pulled by vacuum through a flat or two dimensional screen 210. The material is deposited on the screen, filling the mold cavity 212. The molds themselves are preferably attached to a rotating drum, the rotating molding drum either rotates clockwise or counterclockwise, depending on the requirement to have the shaped side of the molded product up or down after transfer out of the molding drum.

Figure 5A:
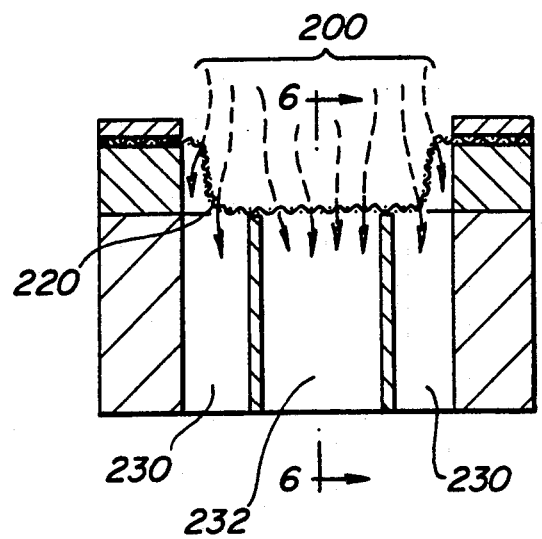
FIGS. 5A–5C depict the process of the present invention using a cross-sectional view of the improved mold cavity and screen of the present invention.
Figure 5B:
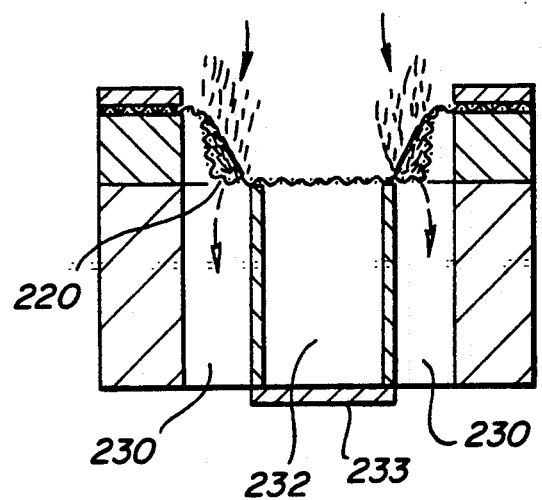
Figure 5C:
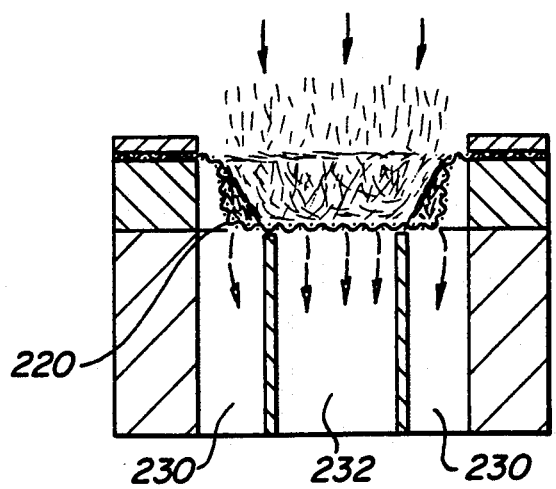

In the present invention, as shown in FIGS. 5A-5C, a three dimensional screen 220 is used and air-entrained material 200 flows through both the bottom and the sides of the screen basket, as illustrated by the arrows. The area under the improved screen 200 is divided into two or more independent suction chambers. As illustrated, the area under the screen is divided into an annular chamber 230, which encircles the perimeter of the area of the molded object. A second chamber 23 is located beneath the central portion of the mold cavity; most preferably this is the location where absorbent material will be selectively deposited. When a vacuum source is applied to a particular suction chamber, preferably at the bottom and/or sides of the mold, air and entrained fibers are selectively pulled to a section of the screen and the material in the air is deposited on that section of screen. As will be apparent to those of ordinary skill, a suction chamber may be routed to any portion of the screen, resulting in the deposition of material anywhere in the surface of a shaped screen. In the example shown in FIG. 5, suction is applied to a first chamber 230, resulting in a buildup of a first material in the mold in the areas above the chamber 230 to which a vacuum is applied. Most preferably, the first material will be a hydrophobic fibrous material. When sufficient amounts of a first material have been deposited, the mold is exposed to continued vacuum in chamber 230 and a positive pressure is applied to another chamber 232. This causes any material inadvertently deposited in the area above the other chamber 232, to be moved to the area above the first chamber 230, thus providing a clearly defined layer of material disposed only on those portions of the screen 220 disposed above a first chamber 230. Suction is then applied to both chambers 230,232. The suction in the first chamber 230 retains the first material in its position. A second material is then deposited in the area above the other chamber 232.

By referring to FIGS. 5A-5C one of ordinary skill can appreciate the novel process of the present invention. As shown by the arrows of FIG. 5A, a first air-entrained material is placed in specified areas of the mold by opening those areas to a vacuum A seal 233 is used to separate other portions of the deposition cavity from the vacuum source. As a result, in a preferred embodiment depicted in FIG. 5B, a portion of the deposition cavity is filled with a first air-entrained material. In the preferred embodiment depicted, a "ring" of hydrophobic material has been airlaid around the perimeter of the deposition cavity.

A second airlaid material is next added to the article, as shown in FIG. 5C. As shown by the arrows, the air-entrained stream is placed in communication with the vacuum source through substantially all the area of the forming cavity. The airflow through the previously airlaid first material keeps that material in place, while the unfilled area is now filled. Thus, in a most preferred embodiment, when the condition shown in FIG. 5C is reached, the article is substantially complete in terms of airlaying and may be removed from further processing.

Figure 8:
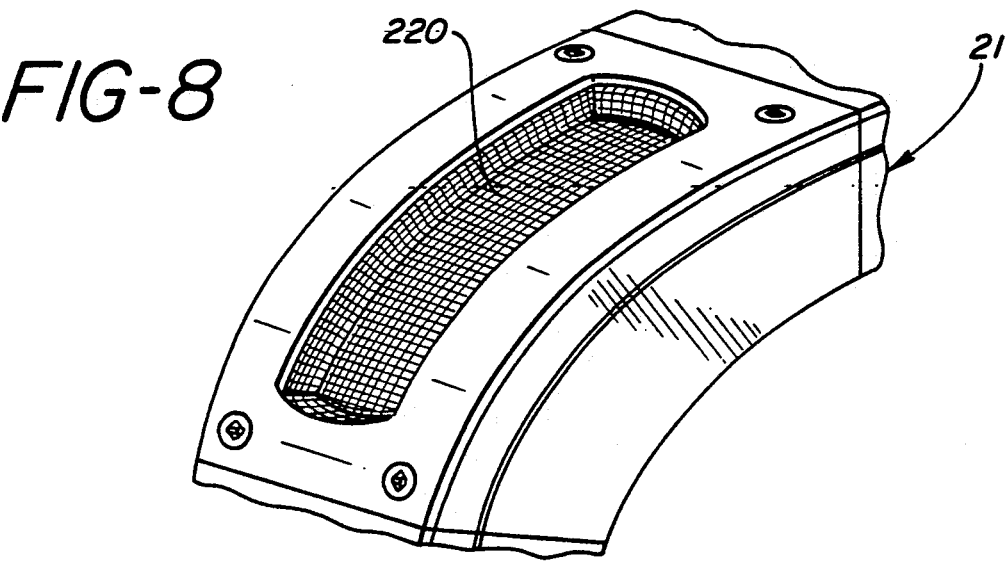
FIG. 8 is a perspective view of the improved mold cavity and screen of the present invention.

Referring now to FIG. 8, there is illustrated a perspective view of a section of the deposition drum showing a typical embodiment of a three dimensional screen 220 made in accordance with certain aspects of the present invention. It can be observed that the foraminous surface of the three dimensional screen 220 covers both the bottom surface and a portion of the side walls, as explained above. Additional details of the airlaying methods of the present invention are discussed both above and below. However, one of ordinary skill will immediately realize that numerous variations of the apparatus and methods of the present invention can be used in combinations to produce an immediate variety of products, all containing two or more distinct materials.

Figure 6:
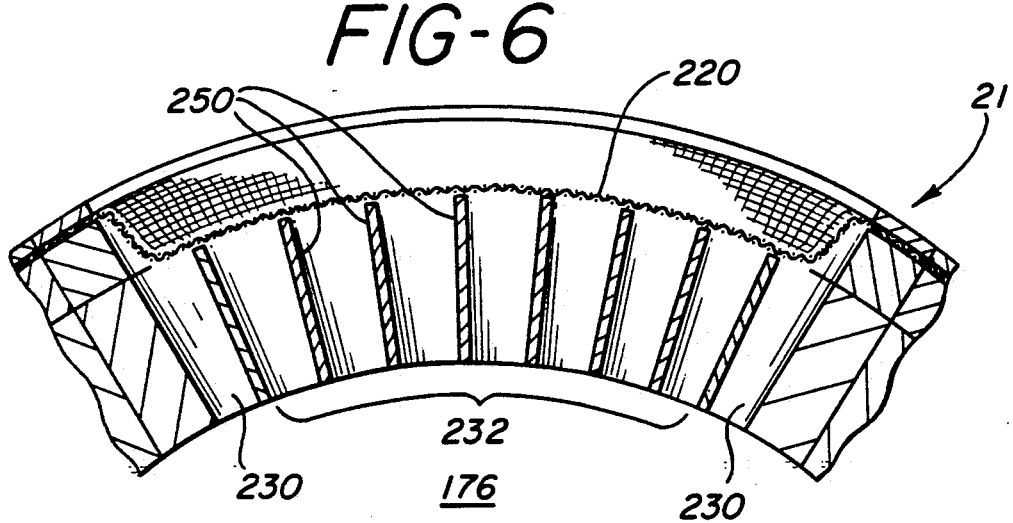
FIG. 6 is a cross-sectional view taken along line 6—6 of FIG. 5A which depicts the structural elements disposed beneath the mold cavity and screen of the present invention.

To place pulps, fibers and other materials within the mold and maintain their placement, it is important to control the airflow through the mold cavity as it enters and leaves a particular forming chamber. In the present invention, as shown in FIG. 6, this is accomplished by a plurality of axial partitions 250 placed beneath the forming screen 220 and extending to and forming the inner sealing surface between the mold cavity 17 and the vacuum chamber 176. In certain embodiments the axial partitions 250 may be comprised of a honeycomb material which has a plurality of axial passages formed therethrough.

The advantages of the basket screen molding of the present invention are that two or more materials may be deposited in selected locations within a molded core and actively removed from all other areas, allowing materials of different properties to be segregated and used optimally. Thus, sharp delineation between the materials which was heretofore impossible is achieved.

Figure 7:
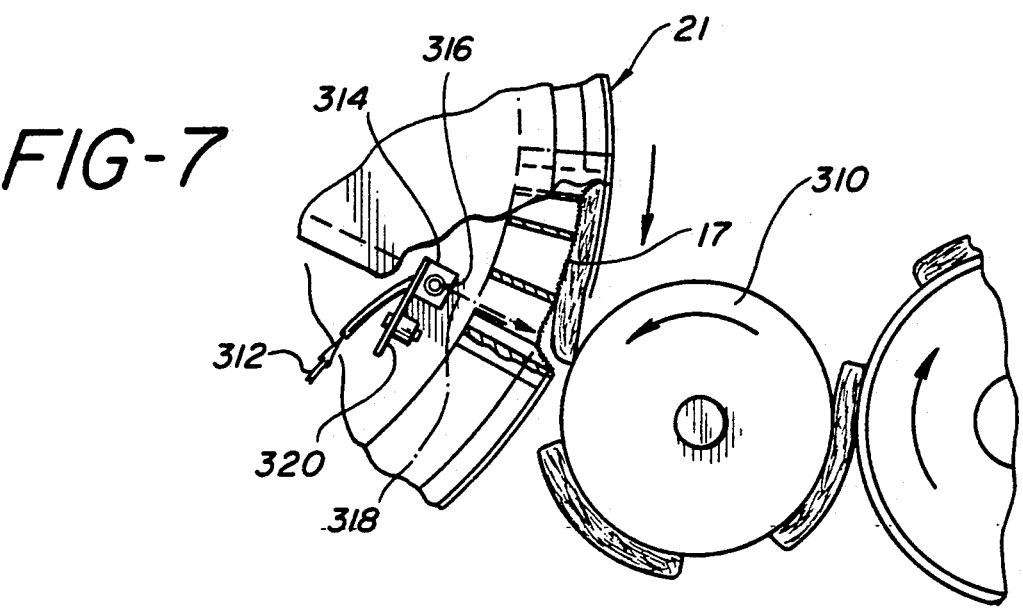
FIG. 7 is a partially broken away view of an airlaying device depicting the fibrous object removal apparatus of the present invention.

To eject formed articles from the mold cavities 17 while avoiding the separation of different layers of formed materials and keeping the article from deforming or separating as it exits the deposition drum 21 to transfer drum 310, apparatus for ejecting a formed article using a precisely controlled stream of air is provided, as illustrated in FIG. 7.

The present invention provides apparatus to feed compressed air 312 into a chamber 314 in which the pressure is distributed evenly (equalized). The air is then forced through a thin adjustable slot 316 providing a knife-like air curtain as shown by the arrow at 318.

Preferably, multi-axis adjustment is provided and the slot opening can be varied from about 0 to about 0.03125 inches. By multi-axis adjustment, it is understood that it may be desireable to precisely direct the stream of air by moving the apparatus along one or more linear axes relative to the molding cavity 17 and/or pivot the apparatus about one or more axes of rotation. The multi-axis adjustment may be provided in many practical ways, well known to those of ordinary skill. For example, certain axes of adjustment may be built into the mounting bracket 320 which affixes the removal apparatus to the deposition drum structure or into the apparatus itself. Preferably, the air knife is operated at a pressure of about 4-20 psi, and most preferably at 12 psi. It has been found that the high velocities created by higher pressures tend to dislodge the fibers of which the article is formed.

The apparatus depicted in FIG. 7 provides a smooth transfer of molded articles onto a vacuum transport device such as a conveyor belt or drum, etc. As depicted, the most preferred transfer device is a transfer drum 310. The air knife depicted in FIG. 7 allows articles formed from two or more distinct layers of fibers to be efficiently removed from the basket molds of the present invention. It has been found that the vacuum transfer drum does not always withdraw the formed article effectively. This is due to fiber entanglement with the sides of the mold cavity, which creates a greater resistance to article removal. The air knife of the present invention thus lifts the leading edge of the article and ensures that it and the rest of the article are transferred smoothly out of the mold.

Although certain embodiments of the present invention have been described with particularity, the invention is by no means limited to the embodiments described. As numerous variations will be immediately apparent to those of ordinary skill, reference should be made to the appended claims to determine the scope of the invention.

What is claimed is:

1. Apparatus for forming fibrous articles having at least two distinct portions of fibrous materials, comprising:
   (a) first means for defiberizing a first fibrous material;
   (b) duct means for entraining and transporting the defiberized first fibrous material to a first airlaying location;
   (c) second means for defiberizing a second fibrous material;
   (d) duct means for entraining and transporting the defiberized second fibrous material to a second airlaying location;
   (e) airlaying apparatus, comprising:
      (i) first forming chamber in communication with a duct means, creating a first airlaying location;
      (ii) second forming chamber in communication with a duct means, creating a second airlaying location;
      (iii) cavity transport means, having an interior section;
      (iv) a plurality of deposition cavities disposed on the cavity transport means, at least a portion of each of the deposition cavities comprising a foraminous surface;
      (v) vacuum chamber means, disposed in the interior section of the cavity transport means, in communication with a least a portion of the foraminous surface of a deposition cavity;

(vi) air handling means for creating a controlled pressure differential between the airlaying locations and the interior section of the cavity transport means; and (f) ejection means for removing a fibrous article from the airlaying apparatus whereby the first defiberized material is deposited in at least a portion of a deposition cavity and the second defiberized material is deposited in at least a portion of the same deposition cavity resulting in an article having at least two distinct portions of fibrous materials having a greater proportion of one of said fibrous materials in one lateral planar portion of said article than in another lateral co-planar portion.

2. The apparatus of claim 1, further comprising environmental control means to regulate the temperature and humidity within the duct means.

3. The apparatus of claim 1, further comprising scarfing means for removing airlaid material extending beyond the boundaries of the deposition cavity, prior to the ejection of the fibrous article.

4. The apparatus of claim 3, further comprising means for collecting the removed airlaid material and transporting it to a duct.

5. The apparatus of claim 1, further comprising:
at least three mill means for defiberizing a fibrous material;
duct means for entraining and transporting the defiberized fibrous material to at least three airlaying locations; and
a plurality of forming chambers in communication with a duct means creating at least three airlaying locations,
whereby fibrous articles having a plurality of distinct portions of fibrous materials are formed.

6. The apparatus of claim 1, wherein the portion of said deposition cavities comprising a foraminous surface is comprised of a surface which forms a major surface of the airlaid article and further comprises at least a portion of the adjacent lateral portion of the cavity.

7. The apparatus of claim 1, further comprising baffle means for regulating the airflow and pressure of distinct portions of said deposition cavities.

8. The apparatus of claim 1, further comprising honeycomb means for channeling the airflow through deposition cavities, the honeycomb means disposed between the foraminous surface of the deposition cavity and the vacuum source.

9. The apparatus of claim 1, further comprising apparatus for creating a positive pressure in a first portion of a deposition cavity and a negative pressure in a second portion of a deposition cavity.

10. The apparatus of claim 1, wherein said first forming chamber deposits airlaid material in a substantially radial manner.

11. The apparatus of claim 1, further comprising a neutral zone chamber within the airlaying apparatus having a circumferential length approximately equal to the length of the deposition cavity, said neutral zone disposed between said first forming chamber and said second forming chamber, the vacuum pressure in the neutral zone being substantially less than the vacuum pressure in said first and second forming chambers.

12. The apparatus of claim 1, further comprising transfer drum means for receiving and transporting the airlaid articles away from the airlaying apparatus.

13. The apparatus of claim 1, further comprising ejector means for removing an airlaid article from within a deposition cavity.

14. The apparatus of claim 13, said ejector means comprising means for controlling a source of compressed air and directing the stream of compressed air against the airlaid article.

15. Deposition cavity apparatus for forming an airlaid article, in communication with a duct carrying a stream of air-entrained fibrous material to an airlaying location, comprising: a frame portion in sealing engagement with the duct; and a foraminous portion, foramen in said foraminous portion being of a size sufficient to retain the air-entrained fibrous materials, whereby an airlaid article is formed in the region of the foraminous portion and further comprising apparatus for creating a negative pressure in a first portion of a deposition cavity and a positive pressure in a second portion of a deposition cavity.

16. A method of forming fibrous articles having at least two distinct portions of fibrous materials, comprising the steps of:
(a) defiberizing a first fibrous material;
(b) entraining and transporting the defiberized first fibrous material to a first airlaying location;
(c) defiberizing a second fibrous material;
(d) entraining and transporting the defiberized second fibrous material to a second airlaying location;
(e) airlaying the fibrous materials by transporting the first fibrous material to a first forming chamber in communication with a duct means, creating a first airlaying location; transporting the second fibrous materials to a second forming chamber in communication with a duct means, creating a second airlaying location; creating a controlled pressure differential between the airlaying locations and a vacuum chamber; passing the first and second air entrained fibers through a deposition cavity, at least a portion of the deposition cavity comprising a foraminous surface; and ejecting the fibrous article from the airlaying apparatus, whereby the first defiberized material is deposited in at least a portion of a deposition cavity and the second defiberized material is deposited in at least a portion of a deposition cavity resulting in an article having at least two distinct co-planar portions of fibrous materials.

17. The method of claim 16, further comprising the step of regulating the temperature and humidity within a duct means.

18. The method of claim 16, further comprising the step of removing airlaid material extending beyond the boundaries of the deposition cavity, prior to the ejection of the fibrous article.

19. The method of claim 18, further comprising the step of collecting the removed airlaid material and transporting it to a duct.

20. The method of claim 16, further comprising the steps of:
defiberizing at least three fibrous materials;
entraining and transporting the defiberized fibrous materials to at least three airlaying locations; and
providing a plurality of forming chambers in communication with a duct means creating at least three airlaying locations,
whereby fibrous articles having a plurality of distinct portions of fibrous materials are formed.

21. The method of claim 16, further comprising the step of regulating the airflow and pressure of distinct portions of said deposition cavities.

22. The method of claim 16, further comprising the step of channeling the airflow through deposition cavities, using means disposed between the foraminous surface of the deposition cavity and the vacuum source.

23. The method of claim 16, further comprising the step of creating a positive pressure in a first portion of a deposition cavity and a negative pressure in a second portion of a deposition cavity.

24. The method of claim 16, wherein said the deposition of material into a first forming chamber is carried out in a substantially radial manner.

25. The method of claim 16, further comprising the step of receiving and transporting the airlaid articles away from the airlaying apparatus.

26. The method of claim 16, further comprising the step of removing airlaid articles from within a deposition cavity.

27. The method of claim 26, wherein said removal step comprises controlling a source of compressed air and directing the stream of compressed air against an airlaid article.

* * * * *